(12) United States Patent
Vitello (10) Patent No.: US 9,402,967 B1
(45) Date of Patent: Aug. 2, 2016

(54) TAMPER EVIDENT CAP ASSEMBLY

(71) Applicant: Jonathan Vitello, Ft. Lauderdale, FL (US)

(72) Inventor: Jonathan Vitello, Ft. Lauderdale, FL (US)

(73) Assignee: Medical Device Engineering, LLC, Pompano Beach, FL (US)

( * ) Notice: Subject to any disclaimer, the term of this patent is extended or adjusted under 35 U.S.C. 154(b) by 0 days.

(21) Appl. No.: 13/736,498

(22) Filed: Jan. 8, 2013

Related U.S. Application Data (63) Continuation-in-part of application No. 12/800,991, filed on May 27, 2010, now Pat. No. 8,348,895.

(51) Int. Cl.
*A61M 5/00* (2006.01)
*A61M 5/50* (2006.01)
*A61M 5/31* (2006.01)

(52) U.S. Cl.
CPC ....... *A61M 5/5086* (2013.01); *A61M 2005/312* (2013.01); *A61M 2005/3104* (2013.01)

(58) Field of Classification Search
CPC .................. A61M 5/5086; A61M 2005/3104; A61M 2005/312; A61M 5/3202; A61M 5/348; A61M 2005/3106; A61M 5/347; A61M 39/1011; A61M 39/20; A61M 2005/3109; A61M 5/50; A61M 2005/3206; A61M 5/3213; A61M 5/3216; A61M 5/34
USPC .......... 215/250, 251, 252, 253; 220/265, 266; 604/111, 200, 256
See application file for complete search history.

(56) References Cited

U.S. PATENT DOCUMENTS

| | | | | |
|---|---|---|---|---|
| 1,970,631 | A * | 8/1934 | Sherman | ................ B65D 41/04 222/498 |
| 2,834,346 | A * | 5/1958 | Adams | .......................... 604/242 |
| 3,245,567 | A | 4/1966 | Knight | |
| 3,706,307 | A | 12/1972 | Hasson | |
| 3,747,751 | A | 7/1973 | Miller et al. | |
| 3,905,375 | A | 9/1975 | Toyama | |
| 4,216,585 | A | 8/1980 | Hatter | |
| 4,216,872 | A | 8/1980 | Bean | |
| 4,313,539 | A | 2/1982 | Raines | |
| 4,420,085 | A | 12/1983 | Wilson et al. | |
| 4,457,445 | A | 7/1984 | Hanks et al. | |
| 4,530,697 | A * | 7/1985 | Kuhlemann et al. | .......... 604/263 |
| 4,571,242 | A | 2/1986 | Klein et al. | |
| 4,667,837 | A | 5/1987 | Vitello et al. | |
| 4,726,483 | A | 2/1988 | Drozd | |
| 4,743,231 | A | 5/1988 | Kay et al. | |
| 4,760,847 | A | 8/1988 | Vaillancourt | |
| 4,832,695 | A | 5/1989 | Rosenberg et al. | |
| 4,844,906 | A | 7/1989 | Hermelin et al. | |

(Continued)

*Primary Examiner* — Kevin C Sirmons
*Assistant Examiner* — William Carpenter
(74) *Attorney, Agent, or Firm* — Malloy & Malloy, P.L.

(57) ABSTRACT

The tamper evident cap assembly is structured for protective connection to a syringe of the type having a nozzle and a discharge port, wherein the cap assembly includes a body configured to receive and restrict access to the nozzle. A flow restricting member is connected to the body in flow restricting relation to the discharge port of the nozzle. An attachment assembly interconnects the body and the flow restricting member and is structured to facilitate detachment of the body from the flow restricting member upon the body being removed from the syringe. A connecting assembly is mounted on the flow restricting member and is structured to be connected to a syringe nozzle by a linearly directed, snap-fit, "push-on" action, and to be disconnected therefrom by a "rotate-off" action.

12 Claims, 3 Drawing Sheets

(56) References Cited

U.S. PATENT DOCUMENTS

| | | | |
|---|---|---|---|
| 5,009,323 | A * | 4/1991 | Montgomery et al. ........ 215/252 |
| 5,049,129 | A | 9/1991 | Zdeb et al. |
| 5,135,496 | A | 8/1992 | Vetter et al. |
| 5,165,560 | A | 11/1992 | Ennis, III et al. |
| 5,328,474 | A | 7/1994 | Raines |
| 5,356,380 | A | 10/1994 | Hoekwater et al. |
| 5,458,580 | A * | 10/1995 | Hajishoreh .............. A61M 5/24 604/110 |
| 5,540,666 | A * | 7/1996 | Barta et al. ..................... 604/192 |
| 5,549,571 | A | 8/1996 | Sak |
| 5,558,648 | A | 9/1996 | Shields |
| 5,624,402 | A | 4/1997 | Imbert |
| 5,702,374 | A | 12/1997 | Johnson |
| 5,776,124 | A | 7/1998 | Wald |
| 5,785,691 | A | 7/1998 | Vetter et al. |
| 5,807,343 | A | 9/1998 | Tucker et al. |
| 5,883,806 | A | 3/1999 | Meador et al. |
| 5,884,457 | A | 3/1999 | Ortiz et al. |
| 5,902,269 | A | 5/1999 | Jentzen |
| 5,951,522 | A | 9/1999 | Rosato et al. |
| 5,951,525 | A | 9/1999 | Thorne et al. |
| 5,989,227 | A * | 11/1999 | Vetter et al. ................... 604/232 |
| 6,000,548 | A | 12/1999 | Tsals |
| 6,021,824 | A | 2/2000 | Larsen et al. |
| 6,027,482 | A | 2/2000 | Imbert |
| 6,068,614 | A | 5/2000 | Kimber et al. |
| 6,126,640 | A | 10/2000 | Tucker et al. |
| 6,190,364 | B1 | 2/2001 | Imbert |
| 6,193,688 | B1 | 2/2001 | Balestracci et al. |
| 6,196,998 | B1 | 3/2001 | Jansen et al. |
| 6,280,418 | B1 | 8/2001 | Reinhard et al. |
| 6,322,543 | B1 | 11/2001 | Singh et al. |
| 6,375,640 | B1 | 4/2002 | Teraoka |
| 6,394,983 | B1 | 5/2002 | Mayoral et al. |
| 6,485,460 | B2 | 11/2002 | Eakins et al. |
| 6,500,155 | B2 | 12/2002 | Sasso |
| 6,520,935 | B1 | 2/2003 | Jansen et al. |
| 6,540,697 | B2 | 4/2003 | Chen |
| 6,565,529 | B1 | 5/2003 | Kimber et al. |
| 6,581,792 | B1 | 6/2003 | Limanjaya |
| 6,585,691 | B1 * | 7/2003 | Vitello ................. A61M 5/3134 215/230 |
| 6,726,652 | B2 | 4/2004 | Eakins et al. |
| 6,726,672 | B1 | 4/2004 | Hanley et al. |
| 6,821,268 | B2 | 11/2004 | Balestracci |
| 6,921,383 | B2 | 7/2005 | Vitello |
| 6,942,643 | B2 | 9/2005 | Eakins et al. |
| 7,141,286 | B1 | 11/2006 | Kessler et al. |
| 7,374,555 | B2 | 5/2008 | Heinz et al. |
| 7,404,500 | B2 | 7/2008 | Marteau et al. |
| 7,425,208 | B1 | 9/2008 | Vitello |
| 7,437,972 | B2 | 10/2008 | Yeager |
| 7,588,563 | B2 | 9/2009 | Guala |
| 7,632,244 | B2 | 12/2009 | Buehler et al. |
| 7,641,636 | B2 | 1/2010 | Moesli et al. |
| 7,735,664 | B1 | 6/2010 | Peters et al. |
| 7,762,988 | B1 | 7/2010 | Vitello |
| 7,918,830 | B2 | 4/2011 | Langan et al. |
| 8,091,727 | B2 | 1/2012 | Domkowski |
| 8,328,082 | B1 | 12/2012 | Bochenko et al. |
| 8,348,895 | B1 | 1/2013 | Vitello |
| 8,353,869 | B2 | 1/2013 | Ranalletta et al. |
| 8,443,999 | B1 | 5/2013 | Reinders |
| 8,579,116 | B2 | 11/2013 | Pether et al. |
| 8,591,462 | B1 | 11/2013 | Vitello |
| 8,597,255 | B2 | 12/2013 | Emmott et al. |
| 8,597,271 | B2 | 12/2013 | Langan et al. |
| 8,616,413 | B2 | 12/2013 | Koyama |
| 8,864,021 | B1 | 10/2014 | Vitello |
| 8,864,707 | B1 | 10/2014 | Vitello |
| 8,864,708 | B1 | 10/2014 | Vitello |
| 9,199,749 | B1 | 12/2015 | Vitello |
| 2002/0023409 | A1 | 2/2002 | Py |
| 2002/0133119 | A1 | 9/2002 | Eakins et al. |
| 2003/0183547 | A1 | 10/2003 | Heyman |
| 2004/0064095 | A1 | 4/2004 | Vitello |
| 2004/0116858 | A1 | 6/2004 | Heinz et al. |
| 2004/0225258 | A1 | 11/2004 | Balestracci |
| 2010/0084403 | A1 | 4/2010 | Popish et al. |
| 2011/0044850 | A1 | 2/2011 | Solomon et al. |
| 2012/0064515 | A2 | 3/2012 | Knapp et al. |
| 2012/0110950 | A1 | 5/2012 | Schraudolph |
| 2013/0018356 | A1 | 1/2013 | Prince et al. |

* cited by examiner

TAMPER EVIDENT CAP ASSEMBLY

CLAIM OF PRIORITY

The present application is a Continuation-In-Part application of a previously filed, and currently pending application, namely, that having Ser. No. 12/800,991 which was filed on May 27, 2010, and which matures into U.S. Pat. No. 8,348,895 on Jan. 8, 2013, with said application being incorporated herein by reference in its entirety.

BACKGROUND OF THE INVENTION

1. Field of the Invention

This invention is directed to a tamper evident cap assembly that is connectable to a fluid loaded syringe in protective, sealing relation to a nozzle and discharge port of a syringe. A body includes a flow restricting member that in the preferred embodiments is interconnected with and defines a one piece construction of the cap assembly. The flow restricting member is structured to facilitate a snap-fit connection of the cap assembly on the syringe, thereby sealing the discharge port thereof. Tampering is indicated by a separation of the flow restricting member and the body, by detachment of the body from the syringe when a predetermined force, sufficient to remove the body from the syringe, is exerted on the body.

2. Description of the Related Art

In hospitals or other medical care facilities, it is very common for medical doctors and other authorized medical personnel to order that a patient be given a drug or medication by injection. In fact, it is currently estimated that more than 16 billion injections are administered on a worldwide basis in any given year.

As a result, it is becoming relatively common in hospital settings for a number of syringes to be pre-loaded or filled by a pharmacist, or other authorized personnel within a hospital or similar facility, at an appropriate location for subsequent dispensing of same to one or more patients. The pharmacy or other location where syringes are filled can and often will be located in a remote part of the hospital, relative to the patient care area where the injection is to be administered. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations are typically located very remote and from a syringe filling station, a loaded syringe is quite often given to another person for delivery to a nurse's station, for subsequent dosing of the patient by qualified personnel. From the foregoing, it may be understood that during the course of loading a syringe with a drug, and also afterwards, when a loaded syringe is delivered to a nurse's station, or even subsequently to a patient, the syringe can easily be handled by more than just one or two people.

Also, and especially in the case of a very expensive drug or an addictive drug, such as but not limited to morphine, there is some danger that a pre-loaded syringe will be tampered with by a person seeking to improperly gain access to the drug, whether to use it himself, or to try to sell it illegally. A resulting danger also exists in that if an unauthorized person were actually to access to the prescribed medicine, he or she might inappropriately substitute saline solution or some other unauthorized substance in the syringe in an effort to avoid detection. By way of example only, if saline solution were substituted for a dose of morphine, this could have extremely serious consequences. Thus, the growing use of syringes which are pre-loaded with a drug presents another problem in that it is important to know if the sealed and/or pre-loaded syringe has, or has not, been tampered with and exposed to contamination or might otherwise have been compromised.

The benefits of using a pre-filled syringe, and of being able to readily determine whether or not it has been tampered with, are abundantly clear. Drugs and medications are specific to each particular patient's disorder or disease being treated. In addition, interactions between drugs and medications given to a patient incorrectly can have serious and deadly consequences. It is, therefore, important to know that a particular medication being injected is, in fact, the drug that was prescribed by the treating physician, and that it has not been replaced by another compound. Moreover, some drugs can have harmful effects in large doses. Accordingly, it is also important to ensure that the proper dosage is followed, as prescribed. Since pre-filled syringes are prepared in advance of being delivered and used, they may be loaded carefully by a pharmacist or other similarly qualified individual to ensure the appropriate medication and dose is prepared. This reduces errors on injection by nurses or physicians who may be in a stressful or time-sensitive situation and may not have the luxury of verifying the correct medication or measuring out a dose, particularly small doses, from a source vial.

Pre-filled syringes are also particularly useful in view of the recent shortage of medications and other injectables, such as narcotics or epinephrine for example. Some drugs and medications, even those which are essential for treating life-threatening diseases, are currently in drastically short supply, due to several factors. For example, during the manufacturing process of some medications, it can occur and has happened for whole batches to become contaminated, such as by bacteria or other microorganisms that could cause infection upon injection, thereby rendering quantities of medications unusable, which in turn, reduces the overall stock of available medications. In addition, manufacturing capacity issues, such the availability and increased cost of raw materials and transportation, as well as lower profit margins, are contributing factors that also result in reduced quantities of medications being produced, and therefore, available to patients. Accordingly, the supply of drugs that are available and safe for use is a starting to be viewed as a precious commodity, with little to no room for waste. The use of pre-filled syringes helps significantly to ensure that only the exact amount of medicine or drugs prescribed are being used, thereby helping to eliminate waste. Also, by having a pharmacist or other qualified person at a filling station preparing the pre-filled syringes, even at a location distant from the patient treatment site helps to ensure that the exact amount of medication needed is delivered. This also circumvents the theft of drugs by "accidental" taking of excess medication, such as to siphon some off for personal use or another non-prescribed purpose, which has unfortunately been known to occur. Accordingly, the use of pre-filled syringes helps maintain the stock of these important drugs so that they may be available to the patients truly in need of them. Further, any unused pre-filled syringes may be recycled so that unused medication does not go to waste. This is only possible, however, if there is some way to determine that a pre-filled syringe has not been tampered with or compromised, thereby verifying the integrity of the contents.

There is has historically been a problem, however, of knowing if a sealed, preloaded syringe has, or has not, been compromised by it being tampered with or might otherwise have a loss of sterility or become contaminated. This and related types of problems have been described in the inventor's own previously granted U.S. Pat. No. 4,667,837 and in other patents, such as U.S. Pat. No. 5,328,474. Despite attempts in the past to prevent unauthorized access to syringe (s) pre-loaded with a drug or medication, it is understood that some problems continue to exist in this field of art and there remains an ongoing need for further improvements, despite the introduction of inventive products according to the above-noted two patents and others.

For instance, there remain problems of manufacturing such products in a manner which is relatively easy and inexpensive, as well as some problems involved with the assembly and placement onto a drug loaded syringe, such as at a drug filling station. Other problems exist relative to maintaining the sterility during storage at the manufacturing facility of the end caps, and during transport of them to a hospital or other medical facility, during storage of them at a hospital or other medical facility, including any transport to a nursing station and ultimately, to a patient care area.

Accordingly, there is a need in this area for an improved tamper evident cap assembly, which is capable of being used with standard or conventional pre-loaded syringes in a manner which overcomes problems and or disadvantages of the type set forth above. If any such improved end cap assembly were developed, it would preferably have certain structural and operative features such as, but not limited to, being at least initially of a one piece construction in order to facilitate appropriate connection to a preloaded syringe. In addition, if any such improved end cap assembly were developed, it would preferably also be structured to provide a clear and unmistakable indication of tampering or of previous access to the contents of the preloaded syringe. Finally, if any such improved, tamper evident end cap assembly were developed, it would ideally also be structurally and operatively reliable, while still remaining relative easy and cost effective to make and assemble, in order to facilitate widespread use and acceptance through out the medical profession. From the foregoing, one might appreciate that the present invention seeks to address such problems, and others, associated with the handling of end caps including, but not limited to, tamper evident caps and luer lock caps during their manufacture, and also during the assembly of them and/or use at different stations and/or by different persons.

SUMMARY OF THE INVENTION

Figure 1:
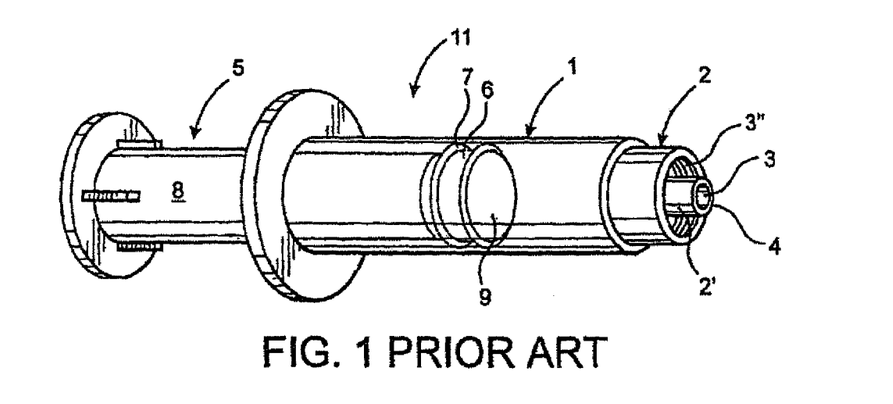
FIG. 1 is a perspective view of a prior art representation of a conventional or standard syringe structure of the type with which the tamper evident cap assembly of the present invention may be used.

The present invention is intended to present a solution to these and other needs which remain in the relevant field of art, and as such, is directed to a tamper evident cap assembly structured for being protectively connected to a syringe of the type including a nozzle and a discharge port, with a representative type of conventional syringe from the prior art being shown in FIG. 1 of the appended drawings. For purposes of clarity, in describing the structural and operative features of the present invention, reference will be made to a conventional or standard syringe 11 of the type represented in FIG. 1. As such, the syringe 11 typically includes a barrel 1 and a nozzle 2. The barrel 1 comprises an elongate interior chamber disposed in fluid communication with an axial passageway or channel 3 on the interior of the nozzle tube or like nozzle portion 2', which may comprise a portion of a luer type fitting. The channel 3 is to be considered a portion of the nozzle 2 and terminates distally at an opening or discharge port 4. A piston 5 is slidable within the barrel and includes a head 6 provided with a circumferential gasket means 7. When assembled, the end face 9 of the head 6 of the piston confronts the interior end of the channel 3 and closes the discharge port 4. The piston also includes a push rod or plunger 8 is connected to the head 6 and is dimensioned to pass into the barrel 1. In use, the standard type syringe 11, after being loaded with its intended contents, is sealed by closing the discharge port 4 with a syringe cap or like closure. Accordingly, the nozzle 2 preferably includes an inner connecting surface 3" or other appropriate connecting structure, such as a ribbed or at least partially threaded surface. Therefore, and for the purpose of fully and accurately describing the tamper evident cap assembly of the present invention, the interior connecting surface or portion 3" and the tube or like nozzle portion 2' are to be considered a part of the nozzle 2.

The tamper evident cap assembly of the present invention comprises a body including a nozzle engaging portion defined by a flow restricting member. When the body is connected to the syringe, the flow restricting member is disposed to restrict fluid flow from the discharge port of the nozzle and is cooperatively structured with a remainder of the body to provide a clear indication of an attempted or accomplished access to the contents of the preloaded syringe. In addition, the body and the flow restricting member are further cooperatively structured in the preferred embodiments to at least initially define a one piece construction of the body and flow restricting member.

The tamper evident cap assembly of the present invention additionally comprises an attachment assembly disposed in interconnecting relation between the body and the flow restricting member. The attachment assembly may include at least one, but possibly a plurality of attachment members disposed in the aforementioned interconnecting relation and which are structured to facilitate disconnection or detachment of the body and the flow restricting member, when a sufficient force is exerted on the body to cause its removal from the syringe. As generally set forth above, the provision of a detachably structured attachment assembly in interconnecting relation between the body and the flow restricting member will preferably also serve to at least initially define a one piece construction of the tamper evident cap assembly. It should be appreciated that the preferred one piece construction will remain intact prior to the removal of the tamper evident cap assembly and/or body from the syringe. However, separation of the body from the flow restricting member and from the syringe nozzle is indicative of attempted access to the contents of the syringe.

In addition, the tamper evident cap assembly also comprises a connecting assembly mounted on the flow restricting member and disposed and structured to retain the flow restricting member on the nozzle of the syringe. As such, the connecting assembly serves to retain the flow restricting member in covering or otherwise flow restricting relation to the discharge port of the nozzle of the syringe, thereby eliminating or restricting the flow of the preloaded drug or fluid within the syringe from exiting through the discharge port. Additional features of the connecting assembly include a cooperative structuring thereof with the nozzle portion of the syringe so as to facilitate a quick, efficient "snap-fit" connection between the flow restricting member and the nozzle. As such, the attachment of the tamper evident cap assembly is significantly facilitated during procedures such as, but not limited to, filling and/or refilling procedures performed by a pharmacist or other authorized personnel. It is generally recognized that individuals involved with the pre-filling operation of the syringe, which may occur numerous times over a given period, already carry out a highly repetitive motion, and can encounter stressful operating conditions if significant handling or manipulation of the syringe is required. Such stressful conditions at least sometimes result in carpel tunnel syndrome or other stress related disorders to the authorized personnel.

Figure 2:
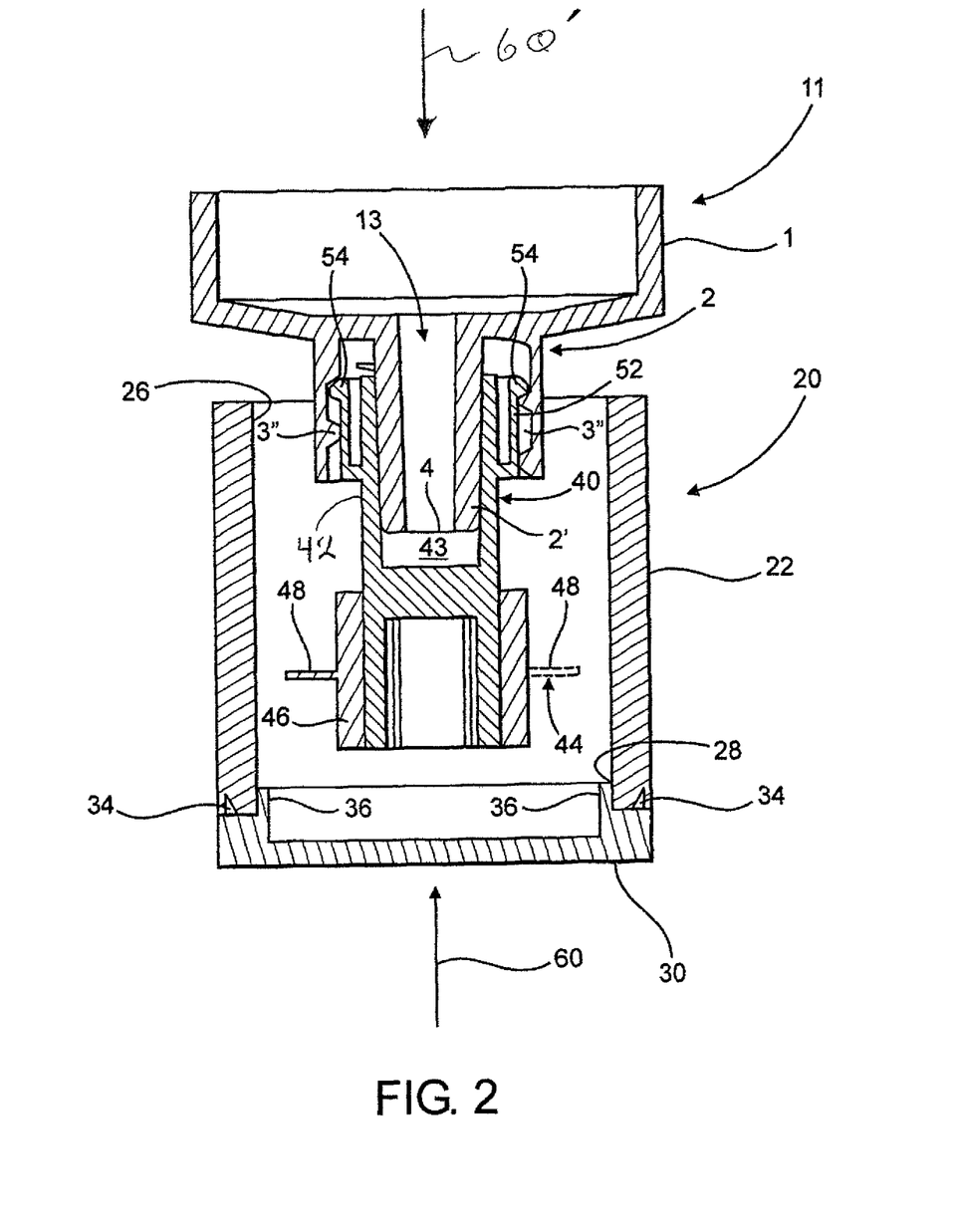
FIG. 2 is a sectional view in partial cutaway of the tamper evident cap assembly of the present invention operatively connected to the nozzle of a prior art or standard syringe, which may be of the type represented in FIG. 1.

Accordingly, the connecting assembly serving to interconnect the flow restricting member and the remaining portions of the body to the syringe is structured to accomplish the aforementioned "snap-fit" connection to a portion of the nozzle of the syringe by substantially linearly directing the cap assembly towards and onto the nozzle portion, when the flow restricting member is substantially coaxially disposed relative to the nozzle. More specifically, the preferred "snap-fit" connection is facilitated due to the provision of a plurality of legs flexibly connected to the flow restricting member. Each of the flexible legs includes a free, distal end having an outwardly projecting lip or like structure formed thereon. Again with reference to the prior art representation of FIG. 1, a linear positioning of the cap assembly of the present invention towards the nozzle 2, while the flow restricting member is substantially coaxially aligned with the interior tube or luer type nozzle portion 2', will cause the plurality of flexible legs to pass into interior, connecting portions of the nozzle 2 and engage the interior connecting surface 3", which, may be ribbed or at least partially threaded or otherwise appropriately structured to interact with the connecting assembly 50 in the intended manner. As a result of such a "snap fit" connection, the connecting assembly will serve to retain the body of the cap assembly and in particular, the flow restricting member, in surrounding, enclosing relation with a portion of the nozzle and in flow restricting relation to the discharge port thereof, as represented in FIG. 2. Therefore, once the tamper evident cap assembly is operatively positioned on the syringe, a predetermined force being exerted on the body, in attempt to remove it from the syringe will be at least partially transferred to the flow restricting member, resulting in a breakage or detachment of the attachment member or members. This in turn will result in a removal or disconnection of the body of the tamper evident cap assembly from the nozzle of the syringe due to the frangible nature or other breakable structure of the attachment assembly. However, due to the retaining engagement of the connecting assembly with the interior, connecting portion of the nozzle, the flow restricting member will remain on the nozzle in flow restricting relation to the discharge port. Such will be a clear indication that attempts have been made to use the syringe and/or access the contents on the interior thereof.

The versatility of the cap assembly is further demonstrated by the structural and operative features of the connecting assembly. Moreover, the cap assembly and in particular, the flow restricting member, are capable of a "push-on/rotate-off" action in order to respectively connect and disconnect the flow restricting member and the nozzle 2. The "push-on" attachment of the flow restricting member and the attached body has been briefly addressed above and will be described in greater detail hereinafter. However, the use of the syringe 11 and/or access to the contents thereof can be easily accomplished by applying a turning or rotating force to the flow restricting member, such as when the body has been removed or detached from the flow restricting member in the manner set forth above. More specifically, the connecting surface 3" may have an at least partially threaded configuration and be cooperatively structured to interact with the connecting assembly. As such, the connecting surface 3" may comprise an internal thread or other appropriate structure which interacts with the connecting assembly of the cap assembly. However, when the aforementioned turning or rotating force is exerted on the flow restricting member in the proper direction, the lip structure(s) on the free distal end of the flow restricting member will be forced along the length of the connecting surface 3" towards the open end of the nozzle 2 and be unthreaded or "unscrewed" therefrom.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 3:
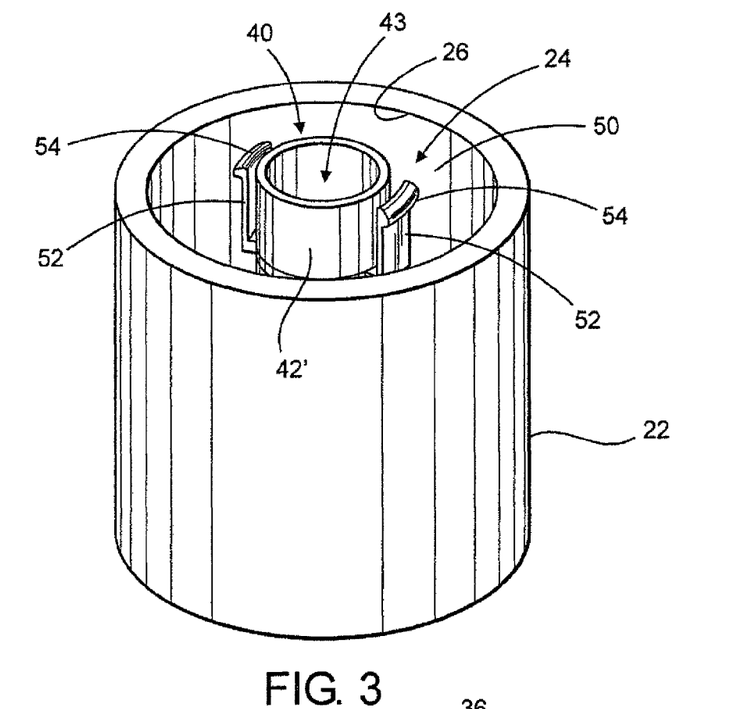
FIG. 3 is a top perspective view of the body portion and a flow restricting member, connected as a one piece construction on an interior of the body, wherein the body is in a non-connected orientation relative to a syringe.
Figure 4:
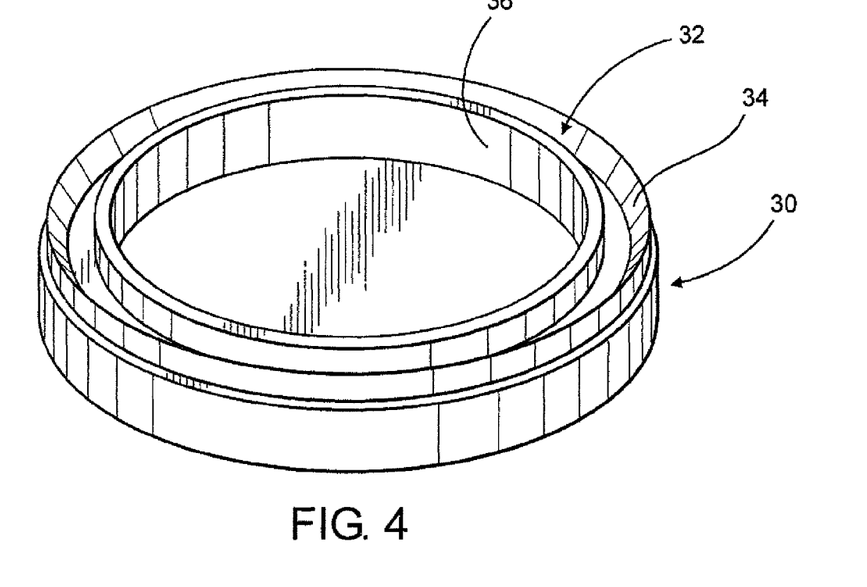
FIG. 4 is a perspective view of a base or end cap of the body of the embodiment of FIGS. 2 and 3.

With primary reference to FIGS. 2-4, the present invention is directed to a tamper evident cap assembly and is generally indicated by reference numeral 20. As set forth above, the cap assembly 20 is intended to be used on or in combination with a conventional or standard type syringe 11, represented as prior art in the above noted embodiment of FIG. 1. It is emphasized that the prior art syringe of FIG. 1 is representative of only one of a plurality of different conventional or standard syringes which may differ from one another in various structural features. However, as will be apparent from the detailed description hereinafter provided, the mounting or connection of the present inventive, tamper-evident cap assembly 20 to the nozzle 2 of the syringe 11, which may comprise a luer type fitting, will prevent fluid discharge from the interior channel 3 and/or discharge port 4. As a result, the flow or discharge of fluid form the interior of the syringe 11 will be prevented, unless the cap assembly 20 is removed from the nozzle 2.

With reference now to FIG. 2, there is shown in a first preferred embodiment a tamper evident cap assembly 20 in an assembled and connected orientation to the syringe 11. Moreover, when operatively connected in the intended manner of FIG. 2, the components of the cap assembly 20 interact with the nozzle assembly 2 not only to restrict access to the contents of the syringe 11, but also to provide a clear indication of such access, whether authorized or not.

Accordingly, and still referring to FIG. 2 as well as FIGS. 3 and 4, the tamper evident cap assembly 20 includes a body 22 having an at least partially hollow interior portion 24 dimensioned to receive the nozzle 2 therein. When the nozzle 2 is disposed within the interior 24, it is substantially surrounded by the cylindrical body 22, when the cap assembly 20 is operatively connected to the syringe 11. As such, the body 22 comprises a substantially cylindrical shell having an open end 26 dimensioned to allow passage therethrough of the nozzle 2 including the nozzle portion or tube 2' shown in FIGS. 1 and 2. As represented, the nozzle portion 2' includes an interior channel 3 disposed in communicating relation with the interior of the barrel 1 of the syringe 11, as set forth above and represented in FIG. 3. The elongated channel 3 terminates in an open discharge port 4 through which fluid, preloaded into the barrel 1 of the syringe 11, may be discharged. The opposite end 28 of the body 22 is closed, as shown in FIG. 2, in order to prevent access to the nozzle 2 or interior 24 of the body 22 when connected to the nozzle 2 in the intended manner.

More specifically, and as is illustrated in FIG. 2 the opposite or distal end 28 of the body 22 is closed through the provision of an end cap member 30, which is shown in FIG. 4. The end cap member 30 may be fixedly connected in closing or covering relation to the distal end 28 of the body, as indicated in FIG. 2. The end cap 30 may be integrally secured to the body 22. However, a preferred embodiment of the tamper evident cap assembly 20 comprises the provision of a continuous, peripheral portion 32 structured to include an outer protruding ring or like member 34. When secured to the body 22, the protruding ring 34 is disposed and structured to fit within a cooperatively dimensioned annular recess formed in the distal end 28 of the body, as also represented in FIG. 2. A secure connection of the end cap 30 on the distal end 28 of the body 22 may be further facilitated by an inner, annular flange 36, shown in FIG. 4, which will be at least partially disposed on the interior of the distal end 28, as also represented in FIG. 2.

Another structural and operative feature of the present invention comprises the provision of a nozzle engaging portion generally indicated as 40 in FIGS. 2 and 3, which is defined by a flow restricting member 42. The nozzle engaging portion 40 and/or flow restricting member 42 is connected directly to the interior 24 of the body 22 by an attachment assembly generally indicated as 44, best shown in FIG. 2. As such, the body 22 and the flow restricting member 42 in the preferred embodiment define, at least initially, a one piece construction which is connectable to the nozzle 2 of the standard syringe 11 as a single, integrated unit. The attachment assembly 44 may include a base 46 which is fixedly connected to a correspondingly disposed portion of the flow restricting member 42. The connection of the base 46 and the flow restricting member 42 may be by an integral attachment, a secure frictional engagement and/or another appropriate fixed securement. Regardless of the specific type of fixed connection between the base 46 and the corresponding portion of the flow restricting member 42, it is again emphasized that the flow restricting member 42 and the body 22 define a one piece construction of the tamper evident cap assembly 20.

Still referring to FIG. 2, additional structural features of the attachment assembly 44 include at least one or alternatively, a plurality of attachment members 48 disposed in interconnecting relation between an exterior of the flow restricting member 42 and an interior surface or other interior portion of the body 22. Moreover, one or more of the attachment members 48 are ideally formed of a frangible material or include other breakable or detachable structures which facilitate(s) a detachment of the flow restricting member 42 from the interior of the body 22 when an adequate or predetermine force is applied to the attachment assembly 44 and/or body 22. Accordingly, when a predetermined force is applied to the body 22 of sufficient magnitude to remove it from the syringe 11, at least a portion of such force will be transferred to the frangible or breakable material attachment member(s) 48. Therefore, attempts to remove the body 22 from the syringe 11, by applying such a predetermined force, will cause a disconnection of the flow restricting member 42 from the interior surface or other interior portion of the body 22, to which it is interconnected.

As represented, the body 22 is primarily, if not exclusively, secured to the nozzle 2 of the syringe 11 by virtue of the interconnection of the attachment assembly 44 between the flow restricting member 42 and the body 22. As a result, a fracturing or breakage of the one or more attachment members 48, due to a sufficient predetermined force being applied thereto, will cause detachment of the body 22 from the nozzle 2 and most probably, a removal of the body 22 from its surrounding, at least partially enclosing relation to the nozzle 2. Moreover, the degree of force required for breakage or detachment of the one or more attachment members 48 is determined and effectively regulated by the material from which the attachment members 48 are formed and/or the number of attachment members utilized. Accordingly, the force required to fracture or break the one or more attachment members 48 should be such as to allow at least a sufficient force to be applied to the body 22 to accomplish its connection, in the intended operative orientation to the nozzle 2, as represented in FIG. 2.

With primary reference to FIGS. 2 and 3, yet additional features of the present invention include a connecting assembly, generally indicated as 50, comprising a plurality of at least two legs 52 each formed of a flexible material and connected to the proximal end 42' of the flow restricting member 42. Each of the legs 52 are disposed on opposite sides of the end 42' of the flow restricting member 42 in preferably opposing relation to one another, as indicated. Moreover, each of the legs 52 include an outwardly projecting or extending lip 54 connected to the free end thereof. Due to the flexibility of the legs 52 and by virtue of the ends to which the lips 54 are attached being "free" or unattached ends, each of the legs 52 will demonstrate a degree of flexibility when disposed into the operative, connected orientation represented in FIG. 2.

The flexible nature of the legs 52 serve to at least partially facilitate a "snap fit" connection between the nozzle 2 and the legs 52 as they pass into the interior of the nozzle 2 and engage connecting portions 3" thereof. Such a snap fit connection is easily accomplished by positioning the tamper evident cap assembly 20 and the nozzle 2 of the syringe 11 in substantially axial alignment with one another, as represented in FIG. 2. Upon accomplishing such alignment, a substantially linearly directed force or "pushing" force 60 is applied to the body 20 in a direction towards the nozzle 2, as schematically indicated. Alternatively, or in combination with the linearly directed and/or pushing force shown by arrow 60, a linearly directed or pushing force 60' may be applied to the syringe 11 in a direction towards the cap assembly 20, as also schematically indicated in FIG. 2. Upon the application of the appropriate force or forces 60 and/or 60', a luer type nozzle 2' will be enclosed within the interior 43 in substantially coaxial alignment with the flow restricting member 42. The provision of the internal connecting portion or surface 3" having an at least partially threaded, ribbed or other appropriate structure, will serve to at least partially retain the lips 54 into retaining engagement with the connecting portion 3". This connection between the flow restricting member 42 and the nozzle 2 will serve to maintain the flow restricting member 42 on the nozzle 2, even when a predetermined force is applied to the exterior of the body 22 in an attempt to remove it and/or the cap assembly 20 from the syringe 11.

As a result of the aforementioned "snap fit" connection, the connecting assembly 50 will serve to retain the body 22 of the cap assembly 20, and in particular, the flow restricting member 42 in enclosing relation with the luer type nozzle portion 2', such that the interior 43 of the flow restricting portion 42 is in flow restricting relation to the elongated channel 30 and in particular, the discharge port 4. Therefore, the interior 43 of the flow restricting member 42 is dimensioned and configured to snuggly receive and sealingly engage the luer lock connector or nozzle portion 2' therein, such that the discharge port 4 is sealed against discharge of the contents of the preloaded syringe 11.

Once the tamper evident cap assembly 20 is operatively positioned on the nozzle 2, as represented in FIG. 2, a predetermined force sufficient to remove the body 22 from the syringe 11, and which is applied to the body 22, will be at least partially transferred to the flow restricting member 40 and to the one or more attachment members 48. Therefore, any force sufficient to accomplish removal of the body 22 will serve to fracture or break the interconnecting attachment members 48, thereby releasing or detaching the body 22 from its enclosing relation to the nozzle 2. However, due to the retaining engagement of the connecting assembly 50 with the interior, connecting surface portion 3" of the nozzle 2, the flow restricting member 42 will remain on the nozzle 2 in flow restricting relation to the discharge 4. As a result, the removal of the body 22 or its disconnection from the flow restricting member 42 will provide a clear indication that access to the interior of the preloaded syringe 11 has been attempted.

The versatility of the cap assembly 20 is further demonstrated by the structural and operative features of the connecting assembly 50. For example, the cap assembly 20 and in particular, the flow restricting member 42 is capable of a "push-on/rotate-off" action in order to respectively connect and disconnect the flow restricting member 42 and the nozzle 2. The "push-on" attachment of the flow restricting member 42 and the attached body 22 is set forth above and represented in FIG. 2 with regard to the application of forces 60 and/or 60'.

However, the use of the syringe 11 and/or access to the contents thereof can be easily accomplished by applying a turning or rotating force to the flow restricting member 42, such as when the body 22 has been removed or detached from the flow restricting member 42, in the manner set forth above. More specifically, and as indicated in FIGS. 1 and 2, the connecting surface 3" may have an at least partially threaded configuration and is cooperatively structured to interact with the connecting assembly 50. As such, the connecting surface 3" may comprise an internal thread or other appropriate structure which interacts with the outwardly protruding lips 54 and the legs 52 to retain the flow restricting member 42 on the nozzle 2. However, when the aforementioned turning or rotating force is exerted on the flow restricting member 42 in the proper direction, the lips 54 will be forced along the length of the connecting surface 3" towards the open end of the nozzle 2 and be unthreaded or "unscrewed" there from.

Since many modifications, variations and changes in detail can be made to the described preferred embodiment of the invention, it is intended that all matters in the foregoing description and shown in the accompanying drawings be interpreted as illustrative and not in a limiting sense. For instance, the present invention has been described as being of a single, one piece construction, but can be arrived at by the connection of or interconnection of various components or pieces or parts to form the components, described herein. Thus, the scope of the invention should be determined by the appended claims and their legal equivalents.

Now that the invention has been described,
What is claimed is:
1. A tamper evident cap assembly operatively connected to a needle-less syringe having a nozzle with interior connecting surface portions and a discharge port formed on the nozzle, said cap assembly comprising:
    a body including a nozzle engaging portion disposed and structured to define a flow restricting member, said flow restricting member disposed within and removably connected to said body,
    said flow restricting member connected to the nozzle in sealing, flow eliminating relation to the discharge port of the nozzle,
    an attachment assembly disposed in interconnecting relation between said body and said flow restricting member,
    said attachment assembly structured to facilitate detachment of said flow restricting member from said body upon said body being removed from the syringe,
    a connecting assembly mounted on said flow restricting member, said connecting assembly disposed and structured to define a linearly directed, snap-fit connection with the syringe and a rotational disconnection with the syringe,
    said connecting assembly comprising a plurality of legs flexibly connected to said flow restricting member; each of said plurality of legs comprising a free distal end and an outwardly projecting lip mounted on said free distal end,
    said snap-fit connection further comprising said plurality of legs disposed within the nozzle and said lips biased in threaded and retaining engagement with the interior connecting surface portions of the nozzle, and
    wherein said attachment assembly is at least partially formed of a frangible material and disposed in detachably interconnecting relation between an interior surface of the body and an outer surface of the flow restricting member.

2. A tamper evident cap assembly as recited in claim 1 wherein said connecting assembly is cooperatively structured with the syringe to accomplish said linearly directed, snap-fit connection upon a substantially linearly directed force being exerted on said body in a direction toward the nozzle or on the syringe in a direction toward said body, said linearly directed force being exerted concurrent to a substantially axial alignment and engagement between said flow restricting member and the nozzle.

3. A tamper evident cap assembly as recited in claim 1 wherein said rotational disconnection is accomplished by a rotational force being exerted on said flow restricting member and a resultant, concurrent forced movement of said lips along and in threaded engagement with the interior connecting surface portions of the nozzle, towards an open end of the nozzle.

4. A tamper evident cap assembly as recited in claim 3 wherein said rotational force is applied directly to said flow restricting member upon detachment thereof from said body.

5. A tamper evident cap assembly as recited in claim 1 wherein at least two legs of said plurality of legs are flexibly connected to said flow restricting member on opposite sides thereof and in substantially opposing relation to one another, said two legs and corresponding ones of said lips biased in threaded and retaining engagement with the interior connecting surface portions of the nozzle to further define said linearly directed, snap-fit connection.

6. A tamper evident cap assembly as recited in claim 5 wherein said flow restricting member is disposed in enclosing relation to the discharge port when said plurality of at least two legs are in said retaining engagement within the nozzle.

7. A tamper evident cap assembly operatively connected to a needle-less syringe having a nozzle with interior threaded connecting surface portions and a discharge port formed on the nozzle, said cap assembly comprising:
- a body including a nozzle engaging portion disposed and structured to define a flow restricting member, said flow restricting member disposed within and removably connected to an interior of said body,
- said flow restricting member connected to the nozzle in sealing, flow eliminating relation to the discharge port of the nozzle,
- an attachment assembly disposed within said body in removably interconnecting relation between said body and said flow restricting member,
- said attachment assembly structured to facilitate detachment of said flow restricting member from said body upon said body being removed from the syringe,
- a connecting assembly mounted on said flow restricting member and structured to define a snap-fit connection with the syringe and a rotational disconnection with the syringe,
- said connecting assembly comprising a plurality of legs flexibly connected to said flow restricting member; each of said plurality of legs comprising a free distal end and an outwardly projecting lip mounted on said free distal end,
- said snap-fit connection comprising said plurality of legs disposed within the nozzle and said lips biased in threaded, retaining engagement with the interior threaded connecting surface portions of the nozzle,
- said rotational disconnection comprising a rotational force exerted on said flow restricting member and a resultant, concurrent forced movement of said lips along and in threaded engagement with the interior threaded connecting surface portions of the nozzle, towards an open end of the nozzle, and
- wherein said attachment assembly is at least partially formed of a frangible material disposed in detachably interconnecting relation between an interior surface of said body and an outer surface of said flow restricting member.

8. A tamper evident cap assembly as recited in claim 7 wherein said rotational force is applied directly to said flow restricting member subsequent to detachment of said flow restricting member from said body.

9. A tamper evident cap assembly as recited in claim 7 wherein said connecting assembly is cooperatively structured with the syringe to accomplish said snap-fit connection upon a substantially linearly directed force being exerted on said body in a direction toward the nozzle or on the syringe in a direction toward said body, said linearly directed force being exerted concurrent to a substantially axial alignment and engagement between said flow restricting member and the nozzle.

10. A tamper evident cap assembly as recited in claim 7 wherein said flow restricting member is disposed exteriorly of and in surrounding, enclosing relation to the discharge port of the nozzle.

11. A tamper evident cap assembly as recited in claim 7 wherein said flow restricting member is connected to the nozzle in the absence of a needle and in sealing, flow eliminating relation to the discharge port of the nozzle.

12. A tamper evident cap assembly operatively connected to a needleless syringe having a nozzle with interior connecting surface portions and a discharge port formed on the nozzle, said cap assembly comprising:
- a body including a nozzle engaging portion disposed and structured to define a flow restricting member, said flow will restricting member disposed within and removably connected to an interior of said body,
- said flow restricting member connected to the nozzle in sealing, flow eliminating relation to the discharge port of the nozzle,
- an attachment assembly disposed within said body in removably interconnecting relation between said body and said flow restricting member,
- said attachment assembly structured to facilitate detachment of said flow restricting member from said body upon said body being removed from the syringe,
- a connecting assembly mounted on said flow restricting member and structured to define a snap-fit connection with the syringe and a rotational disconnection with the syringe,
- said connecting assembly comprising a plurality of legs flexibly connected to said flow restricting member; each of said plurality of legs comprising a free distal end and an outwardly projecting lip mounted on said free distal end,
- said snap-fit connection comprising said lips biased in retaining engagement with the interior connecting surface portions of the nozzle,
- said rotational disconnection comprising a rotational force exerted directly on said flow restricting member and a resultant, concurrent forced movement of said lips along and in threaded engagement with the interior connecting surface portions of the nozzle, towards an open end of the nozzle, and
- wherein said attachment assembly is at least partially formed of a frangible material disposed in detachably interconnecting relation between an interior surface of said body and an outer surface of said flow restricting member.

* * * * *